United States Patent
Lathrop et al.

(10) Patent No.: US 10,136,808 B2
(45) Date of Patent: Nov. 27, 2018

(54) OPTICAL COHERENCE TOMOGRAPHY AS A RAPID, ACCURATE, NON-CONTACT METHOD OF VISUALIZING THE PALISADES OF VOGT

(71) Applicant: University of Pittsburgh—Of the Commonwealth System of Higher Education, Pittsburgh, PA (US)

(72) Inventors: Kira Lynn Lathrop, Glenshaw, PA (US); Joel Steven Schuman, New York, NY (US); Lawrence Edward Kagemann, Silver Spring, MD (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/676,067

(22) Filed: Aug. 14, 2017

(65) Prior Publication Data
US 2017/0367573 A1    Dec. 28, 2017

Related U.S. Application Data

(62) Division of application No. 14/001,753, filed as application No. PCT/US2012/027268 on Mar. 1, 2012, now Pat. No. 9,980,641.
(Continued)

(51) Int. Cl.
A61B 3/00    (2006.01)
A61B 3/14    (2006.01)
(Continued)

(52) U.S. Cl.
CPC ............ *A61B 3/102* (2013.01); *A61B 3/0025* (2013.01); *A61B 3/0041* (2013.01); *A61B 3/14* (2013.01);
(Continued)

(58) Field of Classification Search
CPC    G02B 27/017; G02B 2027/014; G02B 27/22; G02B 2027/0138;
(Continued)

(56) References Cited

U.S. PATENT DOCUMENTS 5,942,487 A      8/1999  Ogawa et al.
6,665,426 B1 *  12/2003  Kim .................. G06K 9/00597
                                                                    382/117
(Continued)

FOREIGN PATENT DOCUMENTS

WO          03065290 A1      8/2003

OTHER PUBLICATIONS

Simm Baharl Ou, International Preliminary Report on Patentability, dated Sep. 3, 2013, 4 pages, The International Bureau of WIPO, Switzerland.

*Primary Examiner* — Brandi Thomas
(74) *Attorney, Agent, or Firm* — Eckert Seamans Cherin & Mellott, LLC; Philip E. Levy

(57) ABSTRACT

The innovation provides for a system and method available to image and visualize the palisades of Vogt via a non-contact process, analyze the image volumes acquired, evaluate the status of the palisades of Vogt from the data represented therein, and display the data in real-time or as a part of a medical record for ongoing consideration and evaluation.

20 Claims, 11 Drawing Sheets

Related U.S. Application Data

(60) Provisional application No. 61/448,389, filed on Mar. 2, 2011.

(51) Int. Cl.
*A61B 3/10* (2006.01)
*G01B 9/02* (2006.01)
*G06T 7/00* (2017.01)
*G06F 19/00* (2018.01)

(52) U.S. Cl.
CPC ..... *G01B 9/02083* (2013.01); *G01B 9/02091* (2013.01); *G06F 19/00* (2013.01); *G06T 7/0012* (2013.01)

(58) Field of Classification Search
CPC ...... G02B 2027/0178; G02B 2027/011; G02B 2027/0116; G02B 2027/0141; G02B 2027/0187; G02B 3/14; G02B 2027/0134; G02B 2027/0174; G02B 27/0093; G02B 27/2221; G02B 27/225; G02B 27/2271; A61B 1/00193; A61B 1/04; A61B 2090/372; A61B 3/102; A61B 5/0091; A61B 5/0507; A61B 5/1077; A61B 5/1114; A61B 5/112; A61B 5/117; A61B 5/1176; A61B 5/4312; A61B 5/4848; A61B 5/6803; A61B 5/742; A61B 5/7445; A61B 90/37
USPC ........ 351/200, 205, 206, 209–211, 221, 222, 351/243–246
See application file for complete search history.

(56) References Cited

U.S. PATENT DOCUMENTS

| | | |
|---|---|---|
| 2006/0154364 A1 | 7/2006 | Coroneo |
| 2006/0215111 A1 | 9/2006 | Mihashi |
| 2009/0271155 A1 | 10/2009 | Dupps, Jr. et al. |
| 2010/0134760 A1 | 6/2010 | Salvati et al. |
| 2011/0151400 A1* | 6/2011 | Boiangiu ............... A61F 2/2803 433/76 |

* cited by examiner

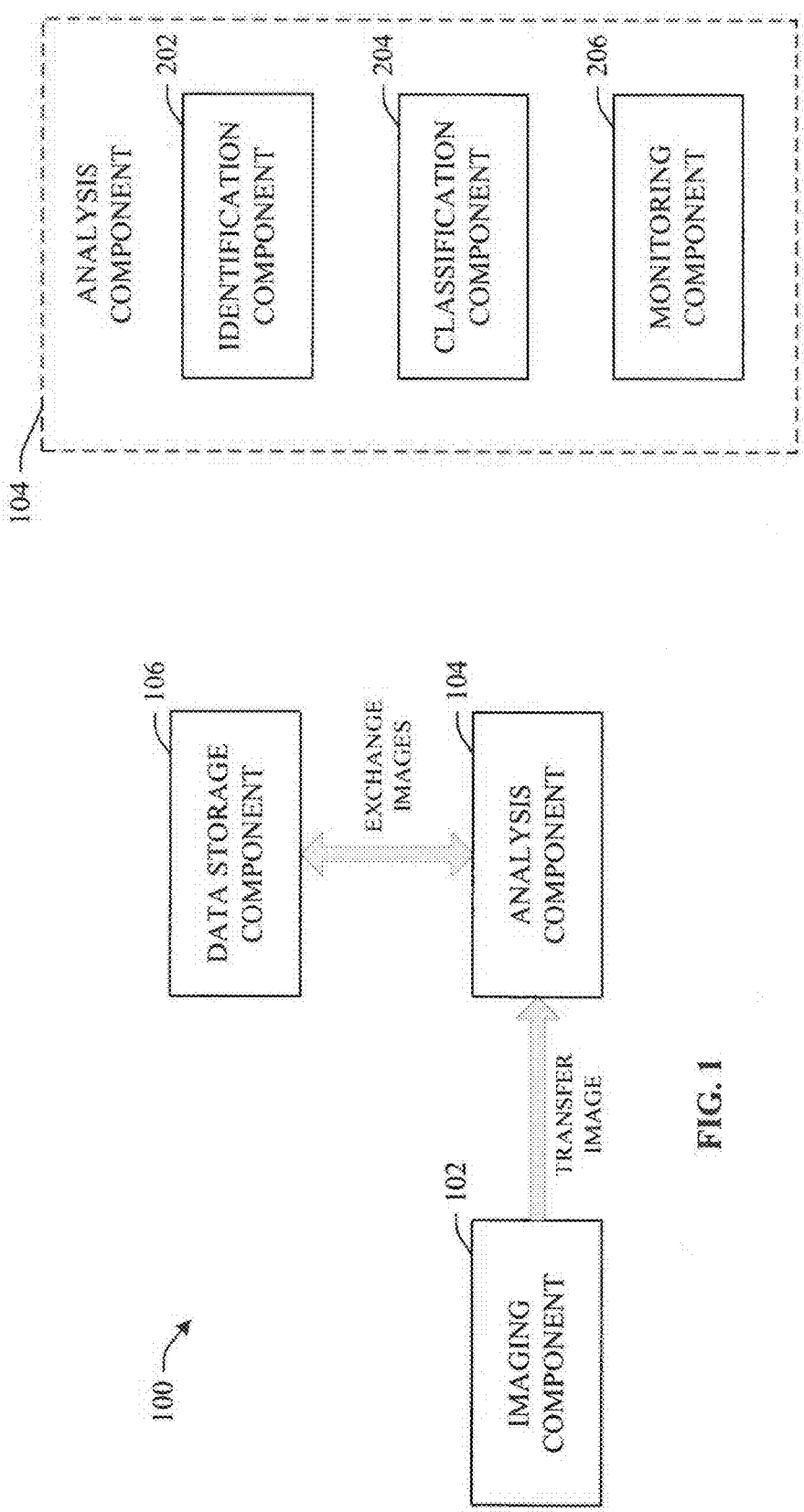

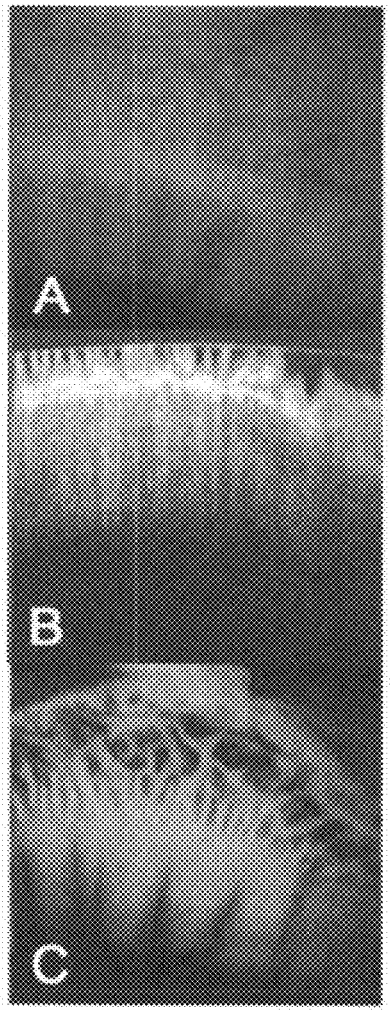 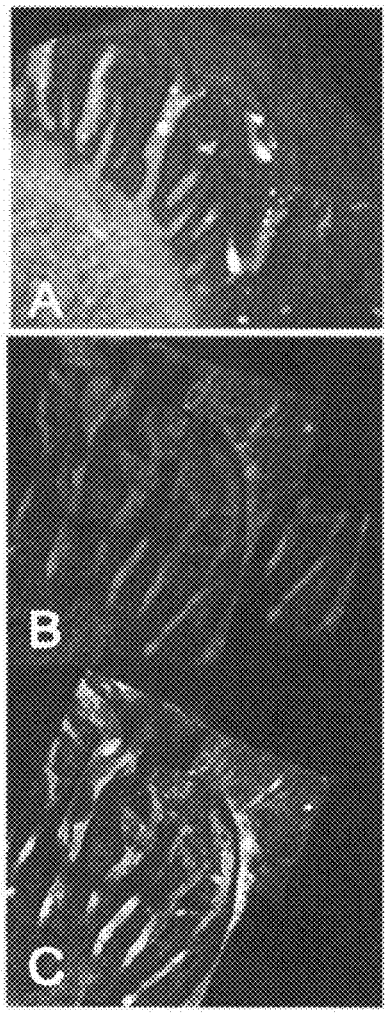
FIGS. 13A-13C　　　　FIGS. 14A-14C

OPTICAL COHERENCE TOMOGRAPHY AS A RAPID, ACCURATE, NON-CONTACT METHOD OF VISUALIZING THE PALISADES OF VOGT

CROSS REFERENCE TO RELATED APPLICATION

This divisional application claims the benefit of co-pending U.S. National Stage patent application Ser. No. 14/001,753 entitled "OPTICAL COHERENCE TOMOGRAPHY AS A RAPID, ACCURATE, NON-CONTACT METHOD OF VISUALIZING THE PALISADES OF VOGT" filed on Nov. 14, 2013 , which claims the benefit of PCT International Application No. PCT/ US 2012/027268 entitled "OPTICAL COHERENCE TOMOGRAPHY AS A RAPID, ACCURATE. NON-CONTACT METHOD OF VISUALIZING THE PALISADES OF VOGT" filed on Mar. 1, 2012, and which claims the benefit of U.S. Provisional Patent Application No. 61/448,389 entitled "OPTICAL COHERENCE TOMOGRAPHY AS A RAPID, ACCURATE, NON-CONTACT METHOD OF VISUALIZING THE PALISADES OF VOGT" filed on Mar. 2, 2011 . The entirety of the above-noted application is incorporated by reference herein.

NOTICE ON GOVERNMENT FUNDING

This invention was made with government support under EY08098 and EY03263 awarded by the National Institutes of Health (NIH). The government has certain rights in the invention.

ORIGIN

The innovation disclosed herein relates to stem cells and more specifically, a system and method to image the palisades of Vogt using Optical Coherence Tomography (OCT).

BACKGROUND

Stem cell deficiency is seen in many ocular diseases and can lead to blindness. The condition is associated with a wide variety of maladies including burns, contact lens wear, dry eye, topical medications, and ocular disease associated with immunologic disorders and can even be seen postoperatively. Treatment of stem cell depletion associated with these conditions has been complicated by the inability to assess the stem cell niche in-vivo. For example, ten million people are bilaterally blinded by conditions with corneal involvement and an additional two million cases of monocular corneal blindness arise each year from trauma. Stem cell therapy and transplantation offers the possibility of cure for many of them.

An instance of one of the stem cell niches is the Palisades of Vogt, a poorly understood structure in the corneal limbus that provides the microenvironment necessary for survival and function of the corneal epithelial stem cells. Considerable variability in the size, shape and specific location of the palisades complicates identification and harvesting of stem cells for transplantation. Indeed, there are changes in the palisades in the normal course of aging as well as during disease conditions. While in-vivo confocal microscopy can be used to identify the palisades, it requires direct contact with the eye, is time consuming and covers a very limited area with each scan.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

In accordance with an aspect of the innovation, a method of visualizing the palisades of Vogt is provided. The method includes imaging the palisades of Vogt via a non-contact in-vivo process; and evaluating the palisades of Vogt image on a display screen or displaying the image in real time to visualize the palisades of Vogt image during medical procedures.

In accordance with another aspect of the innovation, imaging the palisades of Vogt via a non-contact in-vivo process is made possible by Optical Coherence Tomography.

In accordance with another aspect of the innovation, a system for imaging palisades of Vogt is provided and includes an imaging component to take non-contact images of the palisades of Vogt, an analysis component to analyze the images, and data storage to store the images in categories for further evaluation, wherein the images are processed to facilitate visualization of the palisades and reconstructed in C-mode slicing or with 3D modeling.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

FIG. 1 is a block diagram illustration of an imaging/analysis system for in-vivo imaging of palisades of Vogt in accordance with aspects of the innovation.

FIG. 2 is a block diagram illustration of an analysis component of the system of FIG. 1 in accordance with aspects of the innovation.

FIGS. 13A-13C are images with Optical Coherence Tomography with C-mode reconstruction in accordance with aspects of the innovation.

FIG. 14A is an image of a 3D reconstruction of an Optical Coherence Tomography volume segmented to isolate the palisades of Vogt in accordance with aspects of the innovation.

FIG. 14B is a 3D confocal volume reconstruction of the same area displayed in FIG. 14A in accordance with aspects of the innovation.

FIG. 14C is a maximum intensity projection of the same stack set used to reconstruct FIG. 14B in accordance with aspects of the innovation.

DETAILED DESCRIPTION

Figure 3:
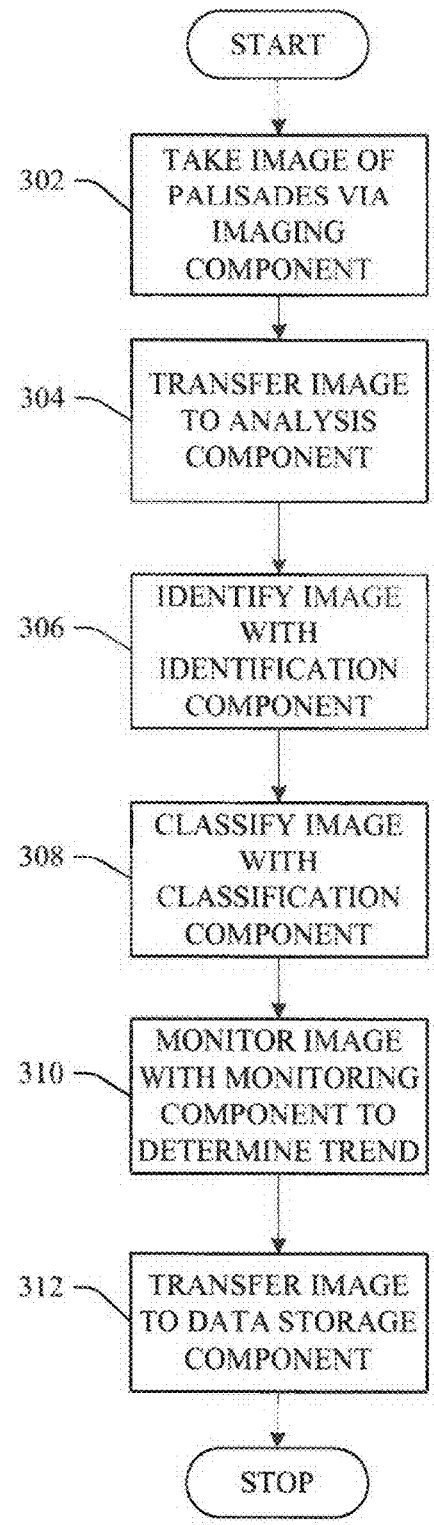
FIG. 3 is a block diagram showing a methodology of imaging and analyzing palisades via Optical Coherence Tomography in accordance with aspects of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

While specific characteristics are described herein (e.g., thickness), it is to be understood that the features, functions and benefits of the innovation can employ characteristics that vary from those described herein. These alternatives are to be included within the scope of the innovation and claims appended hereto.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

Referring now to the figures, FIG. 1 is a block diagram illustration of an example system 100 for imaging and analyzing palisades of Vogt (hereinafter "palisades") via Optical Coherence Tomography (hereinafter "OCT"). OCT provides a first opportunity for rapid, non-contact, three-dimensional in-vivo imaging of the palisades. Development of this technique will provide a vehicle to accurately harvest or deliver stem cells for transplantation, to monitor the palisades clinically for better diagnosis, follow-up and staging, and to identify patients at risk for stem cell deficit early in the disease process. The technique will also provide an additional vehicle for the study of the palisades and for research into ocular diseases. The system 100 includes an imaging component 102 (e.g., OCT component) that provides an image of the palisades, an analysis component 104 to analyze the OCT image, and data storage component 106 to store results from the analysis component 104.

As will be described further below, the OCT component 102 takes images of the palisades for further evaluation. The OCT images of the palisades are transferred to the analysis component 104 for further processing. For example, the analysis component 104 may identify, classify, monitor, etc. palisades in the images as will be described below with reference to FIG. 2. The analysis component 104 communicates with the data storage component 106 to exchange the palisades images or information relating to the palisades images.

The data storage component 106 stores the images for further retrieval and evaluation. For example, the data storage component 106 may store the images in categories or classifications, such as but not limited to, healthy, unhealthy, demographics (e.g., gender, age, race, etc.), etc. Further, the data storage component 106 may break down each category into sub-categories. For example, the unhealthy category may include specific health related sub-categories.

Referring to FIG. 2, the analysis component 104 includes an identification component 202 to identify suitable images, a classification component 204 to classify and categorize the images, and a monitoring component 206 to monitor changes in the image as compared with other sets to determine the status of the palisades. The identification component 202 identifies each palisades image transferred from the OCT component 102 to determine a status of the image. For example, the identification component 202 can determine if the palisades image reflects healthy or unhealthy or if the image indicates that the tissue would be suitable for donation, etc. In order to do so, the identification component 202 can reference information (e.g., images) from a volume of images to make appropriate comparisons and proper identifications.

The classification component 204 can classify each palisades image in categories that correspond to those of the data storage component 106 prior to transferring the image to the data storage component 106. It is to be appreciated that the images need not be classified prior to storage in the data storage component 106. The data storage component 106 can simply store the image in a non-classified category to await further processing and/or classification. Once the images are classified, they are transferred to the data storage component 106 for storage until needed. The classification component 204 can classify automatically or manually. In regards to automatic classification, the classification component 204 can learn how to automatically classify images based on images already stored in the data storage component 106. In other words, the classification component 204 can compare a new image to images stored in the data storage component 106 to determine which category the images belong.

Manual classification can be performed by any qualified person (e.g., doctor, medical technician, etc.) who can identify normal and abnormal characteristics of the palisades. For example, during manual classification, the qualified person can further identify certain abnormalities that cannot be detected automatically. These images can be classified in specialized categories that may warrant additional research.

The monitoring component 206 can monitor the trend (e.g., health) described by the images. For example, multiple images of a particular patient can be taken over a given time period. As each image is taken and transferred to the analysis component 104, the monitoring component 206 can compare the new image with one or more previous images from the patient to determine a trend. For example, does the trend indicate that the patient is improving, staying the same or getting worse. Further, the monitoring component 206 can be used for onscreen evaluation or can be used to project images on a display screen or on the surface of the eye in real-time during surgical/medical procedures.

Referring to FIG. 3, a method of imaging and analyzing via OCT will now be described. At 302, an image of the palisades of Vogt is taken via the OCT component 102 by the method described below. At 304, the image is transferred to the analysis component 104. At 306, the identification component 202 identifies the elements within the image by referencing information (e.g., images) from a volume of images to make appropriate comparisons and proper identifications. At 308, the classification component 204 classifies, automatically or manually, the image into a category corresponding to categories in the data storage component 106. At 310 the monitoring component 206 evaluates the image against stored images to determine a trend, as described above. At 312, the image is transferred to the data storage component 106 and stored in a category as described above for further processing and/or evaluation.

Figure 4A:
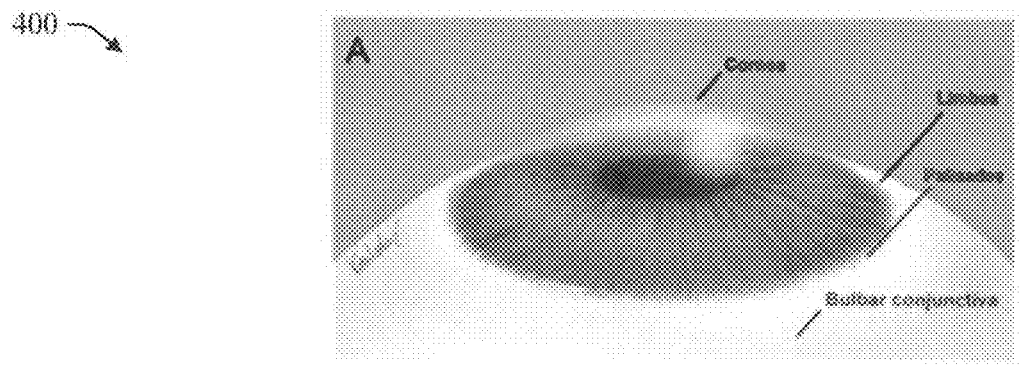
FIGS. 4A-4C are images of an eye and the palisades of Vogt in accordance with aspects of the innovation.
Figure 4B:
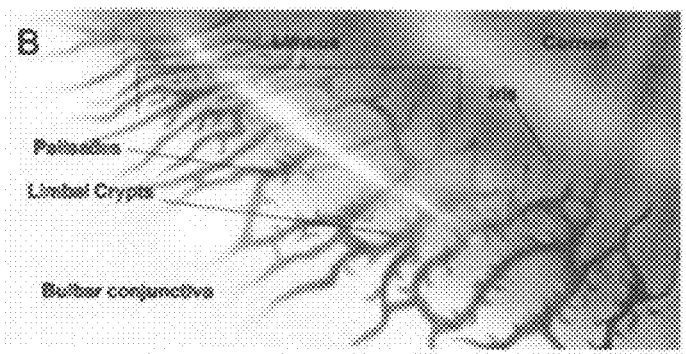
Figure 4C:
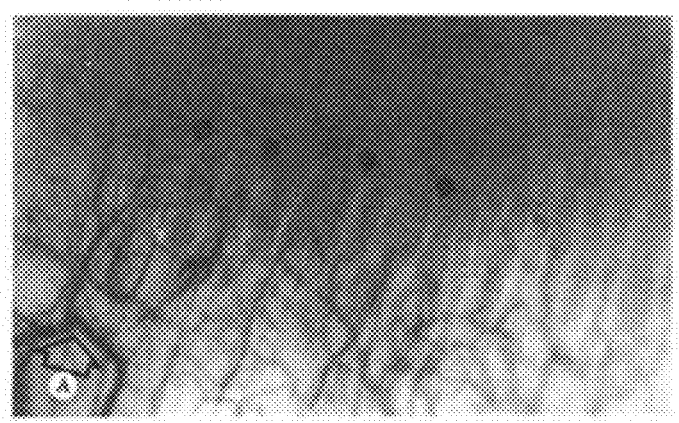

As mentioned above, development of OCT will provide the means to accurately harvest stem cells for transplantation, to monitor the palisades clinically for better diagnosis, follow-up and staging, and to identify patients at risk for stem cell deficit early in the disease process. Stem cells require a highly specialized environment which can provide protection and nutrition for the cells and access to the tissue that they support. FIGS. 4A-4C are images 400 of an eye showing a region between the cornea and the sclera, known as the limbus, that provides this specialized environment, known as the palisades of Vogt. Stem cells in the limbus produce cells which migrate to the epithelial surface and the move toward the center of the cornea. The corneal epithelium is in a constant state of renewal with complete turnover of the cell population every five to seven days. This dynamic, rapid renewal is necessary to maintain the transparent, avascular, highly organized tissue of the cornea.

The palisades are regarded as the putative limbal epithelial stem cell niche. Although, first noted in 1866 and described in detail in 1921, the palisades remain a poorly understood and elusive region. Because their function was not clear, there was no strong motivation to clearly describe the palisades. Rapid progress in stem cell research, however, has directed more attention toward the palisades as numerous investigations point to the palisades as the location of corneal stem cells that maintain corneal epithelial homeostasis and clarity. Ideally the corneal stem cells would be visualized directly, but in the absence of such technology, the palisades can be used to determine the general location and status of the stem cells. The difficulty in defining the palisades arises from their unique structure, configuration and dimension in each individual and from the fact that they are difficult to visualize. Deeper understanding of the palisades is crucial to developing new stem cell therapies targeted at restoring vision and maintaining the health of the eye, for without the environment provided by the limbal palisades there are no limbal stem cells to sustain the cornea. The convergence of progress in the development of OCT, advances in 3-dimensional stitching and rendering techniques and improvements in immunofluorescent staining and microscopy now offer the opportunity to reexamine the structure of the palisades in general and to visualize the full structure of the palisades in-vivo for the first time.

Still referring to FIGS. 4A-4C, the palisades, which have a structure as unique as fingerprints, reside in a 1-2 mm band of the connective tissue primarily in the superior and inferior regions of the corneoscleral limbus and follow an irregular and undulating radial pattern around the cornea. The conjunctival epithelium becomes thickened in this area and forms radial zones called interpalisades or epithelial rete ridges. Thus, the epithelium comes into direct contact with the palisade region. Terminal capillaries from the anterior ciliary arteries make this region a rich, stable environment for stem cells. The size, shape and configuration of the palisades changes over time in response to acquired or congenital conditions, aging, surgery and medication. Destruction of the palisades and the associated destruction of the stem cells they contain results in conjunctivalization of the cornea, vascular invasion and concomitant blindness. Restoration of the palisades and their resident stem cells results in clearing of the cornea and restoration of vision.

Visualization of portions of the palisades is sometimes possible using a slit lamp and can be enhanced by fluorescein imaging. However, in up to 20% of patients palisades cannot be identified clinically using current methods and none of these techniques give an overall view of the dimension and structure of the whole palisade region. Confocal microscopy has been used to visualize and characterize changes in the palisades associated with age and to retrieve targeted biopsies which produce higher yields of stem cells. Confocal microscopy has also been proposed as a technique to monitor the status of keratolimbal allografts following transplantation. The technique, however, is limited by high magnification which restricts the area of the scan. In addition, in-vivo confocal microscopy requires direct contact with the eye and anesthesia, either of which may inadvertently cause more damage to an eye that has already suffered insult. Further, relatively long periods of time are required for scans of small portions of the eye and the quality of the scans may be compromised by blinking, anxiety and involuntary motion.

Figures 5A, 5B, 5C, 5D, 5E, 5F, 5G, 5H:
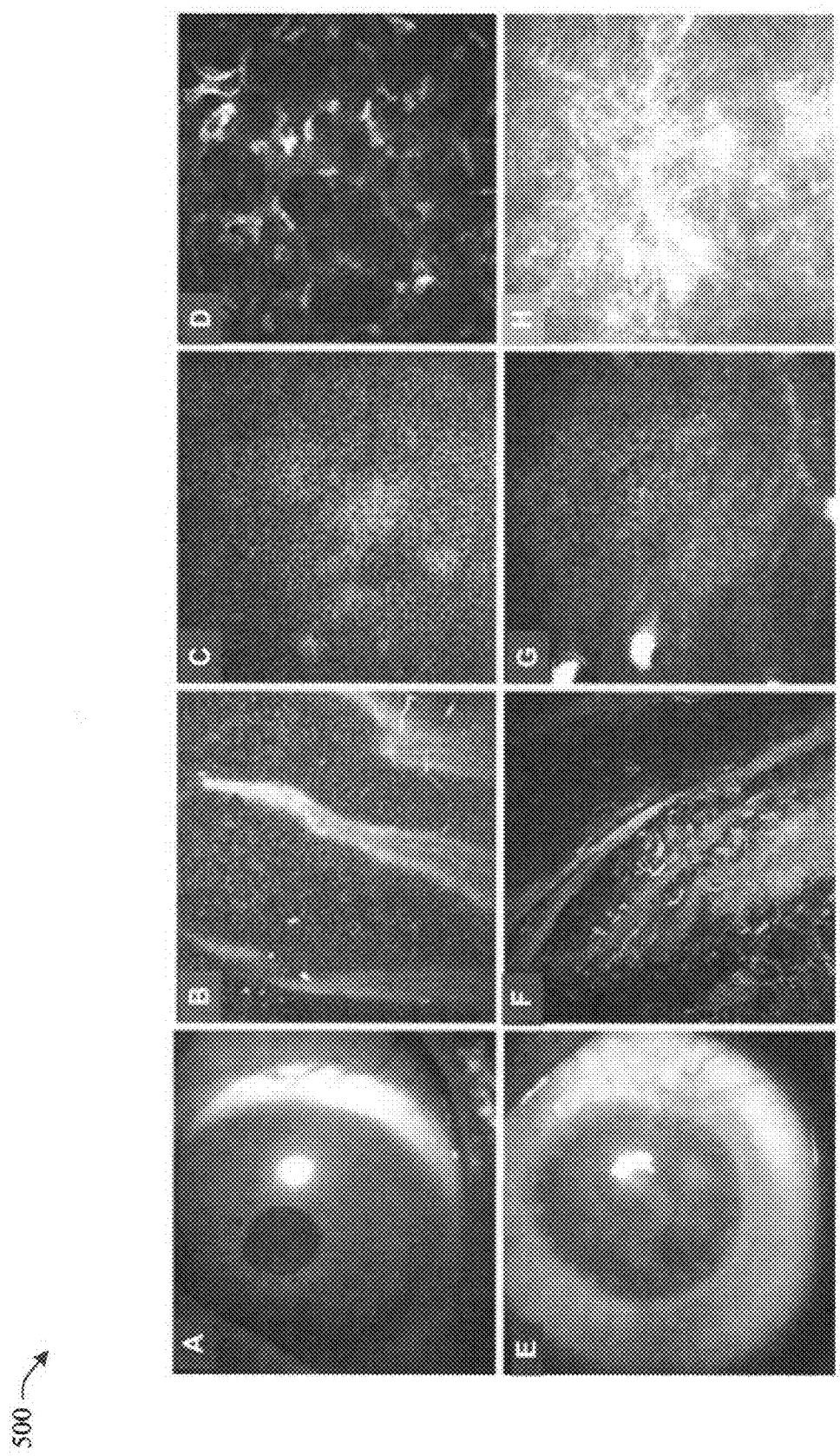
FIGS. 5A-5H are images comparing an ocular surface in a surviving and failed keratolimbal allograft in accordance with aspects of the innovation.

For example, FIGS. 5A-5H compare images 500 an ocular surface in a surviving (FIGS. 5A-5D) and failed (FIGS. 5E-5H) keratolimbal allograft. FIG. 5A shows a slit-lamp photo of a transparent cornea with a few vessels at the limbus. In FIG. 5B, the palisades, denoted by the blue arrow, extend into the limbal epithelium in a regular arrangement, with slender vessels inside. Further, only a few dendritic cells were detected and are denoted by the red arrow. Finally, FIG. 5B illustrates that the morphology of the limbalepithelial cells was normal. FIGS. 5C and 5D illustrate central corneal cells displaying a polygonal shape and a regular arrangement, and that the morphology of the central stromal cells was normal respectively.

FIG. 5E shows a slit-lamp photo of a failed graft showing an opacified cornea with neovascularization. FIG. 5F shows that the palisades were destroyed and that the stromal process was thin and irregular. Further, a large number of dendritic cells, denoted by the blue arrow, were detected. FIG. 5E also shows that the epithelial cells between stromal process had relatively large cell bodies, denoted by the red arrow. FIGS. 5G and 5H show that the central corneal epithelial cells were larger and that the central corneal stroma was hyperreflective respectively.

Loss of the palisades may be partial or complete and may be caused by acquired or congenital conditions and may present as the primary or secondary issue. Limbal epithelial stem cell deficiency (LSCD) refers to the spectrum of conditions which cause loss of stem cells and the palisades. Patients with LSCD may experience significant pain, severe vision loss and photophobia. Included in causes of LSCD are: keratolimbal allograft transplantation, acid and alkali burns, thermal burns, Stevens-Johnson syndrome, ocular cicatrizing pemphigoid, multiple surgeries, contact lens wear, microbial infections, ocular surface disease, topical medications, ultraviolet and ionizing radiation, aniridia, congenital erthrokeratodermia, keratitis associated with endocrine deficiencies, neurotrophic keratopathy, chronic limbitis, peripheral ulcerative disorders, pterygium, chronic bullous keratopathy, severe dry eye, Peters anomaly, ecdodermal dysplasia, long-term use of topical medications including antibiotics, corticosteroids, B-blockers, pilocarpine, mitomycin-C. Other diagnoses that may contribute to stem cell failure include keratoconjunctivitis sicca, rosacea, and HSV keratitis.

Prior to 1989 treatment for total LCSD was limited to penetrating keratoplasty, tarsorrhaphy and the use of artificial tears, none of which address the cause of the disease. With the advent of keratolimbal allograft transplantation it has become possible to not only treat the cause of LCSD but in some instances, to cure the disease. Continued progress in the field has produced methods of cultivating and expanding stem cells ex-vivo to reduce the size of the tissue that must be harvested. This is particularly important in the case of autografts because harvesting a large an area of the limbus from the donor eye may produce LCSD in that eye, thus compromising the good eye in an effort to rescue the afflicted eye. Autografts remain the most desirable transplant because they do not require the patient to maintain immunosuppressive therapy following surgery. In instances where the LCSD is not total there are more treatment options.

Allografts from living relatives or cadavers may also be used, although the success rate is not as high. In some instances of allograft from close relatives the match may be good enough that immunosuppression is not required. Graft rejection remains a major concern for patients with severe disease. Development of enhanced transplant techniques continues and includes design of new synthetic scaffolds to maintain and support the cells during transplantation or use of amniotic membrane as a substrate. Each of these techniques has advantages and drawbacks, but all of them would benefit from an accurate, non-contact way to monitor pre and post-surgical progress.

Progress in understanding the nature of stem cell niches has been hampered by the fact that it has not been possible to observe and monitor adult stem cell niches in-vivo. Previous 3D reconstructions of the palisades have been conducted ex-vivo with confocal imaging. In these studies, the corneal epithelium is used as a locator for the roof of the palisade structure, but the structure itself is not clearly defined.

OCT was invented in 1991 and was initially used to image the retina. In 2001 the first anterior segment OCT was used to investigate anterior chamber and cornea. Recent advances in OCT technology allow acquisition of scans at ultrahigh speeds up to 400,000 axial scans per second. This non-contact technique allows internal structures to be imaged in biological tissues in-vivo by measuring the delay caused by reflection of light from the sample. High-resolution images with exquisite detail are acquired rapidly and at a comfortable working distance from the patient by using long-wavelength laser light. Recognition of tissue boundaries depends on contrast between backscattered or reflected signal strength.

OCT has never been described as a method to visualize the pattern of the palisades until a recent pilot study in which a Cirrus high definition (HD)-OCT system and a modified Bioptigen spectral-domain optical coherence tomography system were used to acquire images of the corneal limbus. The purpose of this pilot study was to demonstrate in-vivo visualization of the palisades in living human eyes using spectral domain (SD)-OCT. The Bioptigen system had 3.0- to 3.5-µm axial image resolution and an imaging speed of 28,000 axial scans per second, and the Cirrus OCT had 5-µm resolution and a speed of 27,000 axial scans per second. 3D image sets were analyzed using C-mode slicing to reconstruct the area of the epithelial basement membrane. Reconstruction of the corneal limbal region via 3D OCT image sets revealed the configuration of the palisades.

Further, the pilot study OCT images clearly showed the epithelium and the epithelial rete ridges extending downward interdigitated by a dense structure. This is completely consistent with the configuration and location of the palisades. Preliminary reconstructions of this area in three-dimensional models reveal a structure with features that correspond to documented images of the palisades including areas that radiate outward from the corneal margin with connections between structures and descending crypt-like structures. These three-dimensional models provide a complex, detailed representation of this unique structure and, not surprisingly, reveal it to be more intricate than previously described. The rapid acquisition of images with OCT allows acquisition of 3D volumes that encompass the entire limbus. Development of analysis tools and software that allow reconstruction of the palisades from the full circumference of the cornea will for the first time allow rapid, non-contact, accurate visualization of the palisades of each individual patient.

Figure 6A:
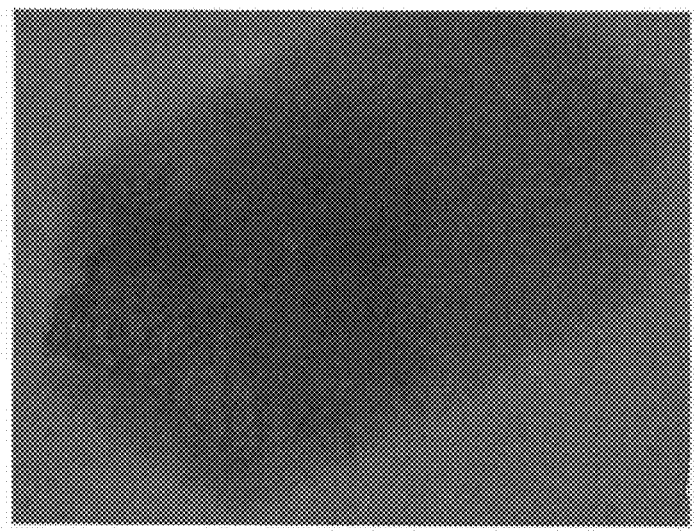
FIG. 6A is a three-dimensional reconstruction of a limbal area showing the palisades of Vogt in accordance with aspects of the innovation.
Figure 6B:
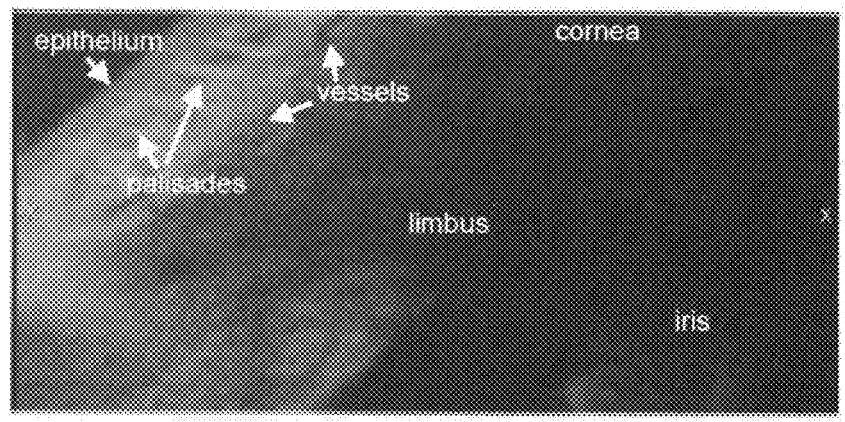
FIG. 6B is one of the planes of the OCT image stack that was used to generate the reconstruction shown in FIG. 6A in accordance with aspects of the innovation.
Figures 7A, 7B, 7C, 7D:
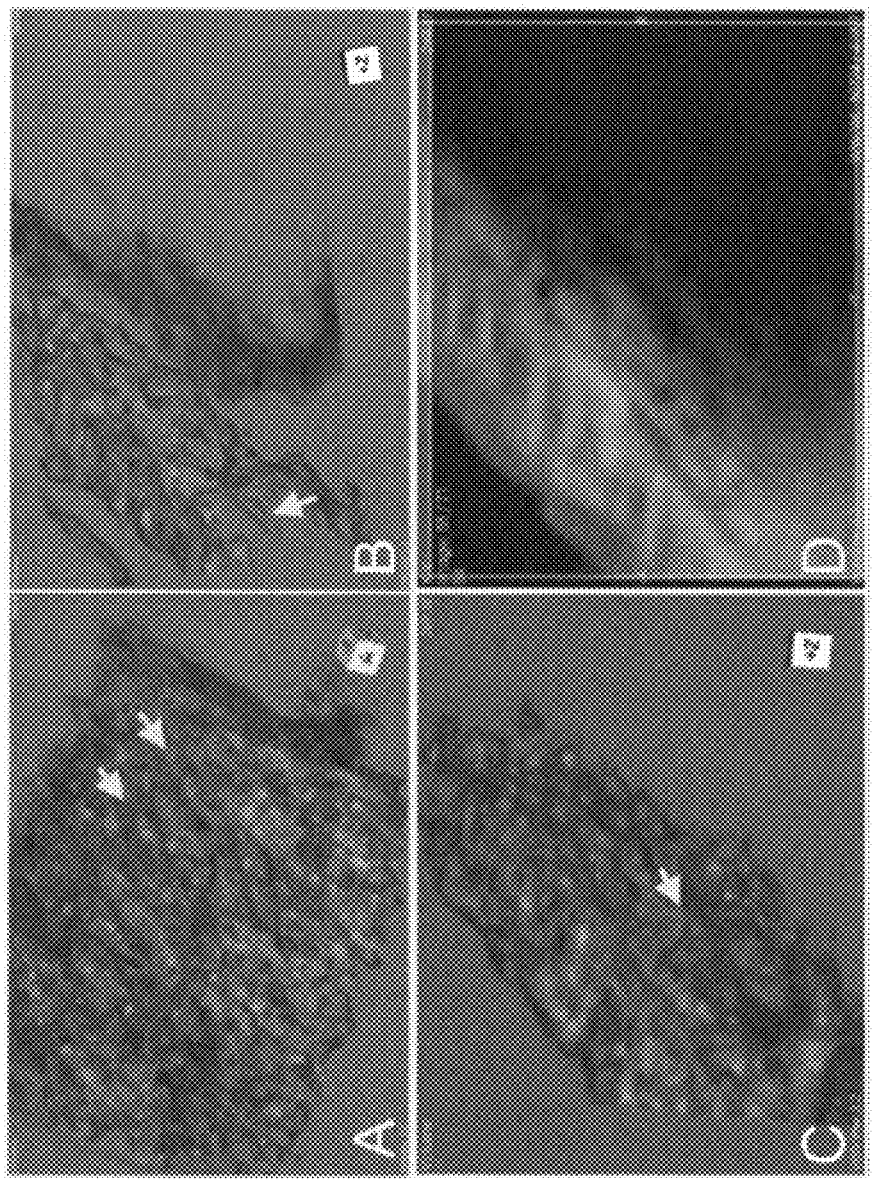
FIGS. 7A-7C are three-dimensional reconstructions of radial ridges extending from a corneal margin in accordance with aspects of the innovation.
FIG. 7D is one plane of the OCT image stack that was used to generate the reconstructions shown in FIGS. 7A-7C in accordance with aspects of the innovation.

For example, referring to FIGS. 6A and 6B, FIG. 6A is an image 600A of a rotated model of the same limbal area image 600B in FIG. 6B. The palisades are shown in magenta and the lower margin of the cornea in blue. Further, referring to FIGS. 7A-7D, images 700 of radial ridges extending from the corneal margin are shown in FIG. 7A. FIG. 7B shows a portion of the same sample pictured from the side. Crypt-like structures extending below a dense mesh can be seen. FIGS. 7C and 7D are the same dataset, whereby FIG. 7C shows the 3D reconstruction of the palisade region and FIG. 7D shows one slice of the original OCT image.

Thus, OCT offers an alternative imaging modality that eliminates all the limitations described above relating to confocal microscopy and other conventional methods. In other words, the innovation disclosed herein establishes that OCT is capable of high-resolution non-contact imaging of the palisades and has distinct advantages over confocal imaging, as will be subsequently described.

Twenty human donor corneal rims were recovered in organ culture chambers containing Optisol GS media as provided by the tissue bank following corneal transplant surgeries. The donor tissues were 24-70 years old and were fixed 2-7 days post-mortem. Epithelium had been removed around the corneal button during the surgery, but was present in the limbal region and conjunctiva.

The rims were imaged with a high-speed ultra-high-resolution OCT scanner using a raster pattern. Scans sampled a 2×2×2 mm region of tissue with 512×180×1024 measurements. The scanner included a 100 nm bandwidth light source centered at 870 nm yielding a coherence length of 2 µm in tissue. Images were reconstructed and processed using spectral OCT (SOCT) browser software developed by others.

Immunolabeling was performed by washing the corneal rims with phosphate buffered saline (PBS) for approximately 15 minutes two times prior to fixation in 4% paraformaldehyde (PFA) for a predetermined time period (e.g., 24 hours) at 4° C. The tissue was washed in PBS-Tx (PBS containing 0.3% triton x-100) for approximately 15 minutes three times and then permeabilized with 0.5% triton x-100 for approximately two hours at room temperature. Following permeabilization, the tissue was washed with PBS-Tx for approximately 5 minutes three times. Blocking was done by using 10% heat inactivated goat serum (containing 0.3% triton x-100) for approximately 2 hours at room temperature. Tissue was then washed with PBS-Tx for approximately 10 minutes at room temperature and incubated with culture supernatants containing primary mouse monoclonal anti-human Type VII collagen antibody 5D2 diluted 1:1 with the blocking buffer at room temperature for approximately 1 hour followed by incubation at 4° C. for a predetermined timer period (e.g., 12 hours). The tissue was then washed with PBS-Tx for approximately 20 minutes 5 times. Alexafluor 488 conjugated goat anti-mouse IgG was used for the secondary antibody and was incubated for two hours at room temperature without light. DAPI or 4',6-diamidino-2-phenylindole (50 ul, 300 nM) was added directly on the secondary antibody for approximately 20 minutes. Finally the tissue was washed with PBS-Tx for approximately 20 minutes three times and was mounted. Large-format spacers for whole mounting human corneal rims were made from shelf liner. One-inch circles were punched with a lever punch and the spacer was fixed to a large format slide with an adhesive. Corneal rims were cut in half and relief cuts were made in the sclera and cornea to allow the rim to lie flat. The corneal rims were placed in the well created by the spacer and Immu-mount was used to fill the well. Large format coverslips were used to seal the mounted specimens. Whole mounting the tissue with spacers offers the distinct advantage of maintaining the morphology of the tissue, which is critical for accurate three-dimensional (3D) reconstruction.

Confocal microscopy was conducted on an Olympus FV1000 inverted laser scanning confocal microscope system with a 20× oil (refractive index 0.85) objective. Image stack acquisition was under sampled in the XY plane and optimized for the Z dimension to allow the best possible reconstructions and to control file sizes and acquisition time. The depth of the stacks ranged from 50-150 microns. Images were saved in the native Olympus Image Binary (OIB) format and subsequently converted to 8 bit RGB (red, green, blue).

Reference image sets of corneal rims whole mounted and immunofluorescently labeled to define the basement membrane of the limbus were acquired with laser scanning confocal microscopy. Large (up to 50) sequential confocal stack sets were stitched together and 3D models were built. This kind of acquisition and reconstruction is not possible in living subjects because of the need for a fluorescent label and the time required for acquisition. 3D display of reconstructed stacks is available as supplementary material. OCT image sets were reconstructed in the SOCT Browser, smoothed with a rolling average and then viewed in a selective en-face mode using C-mode slicing. The confocal and OCT image sets were correlated to identify the same palisade structures.

Figures 8A, 8B, 8C:
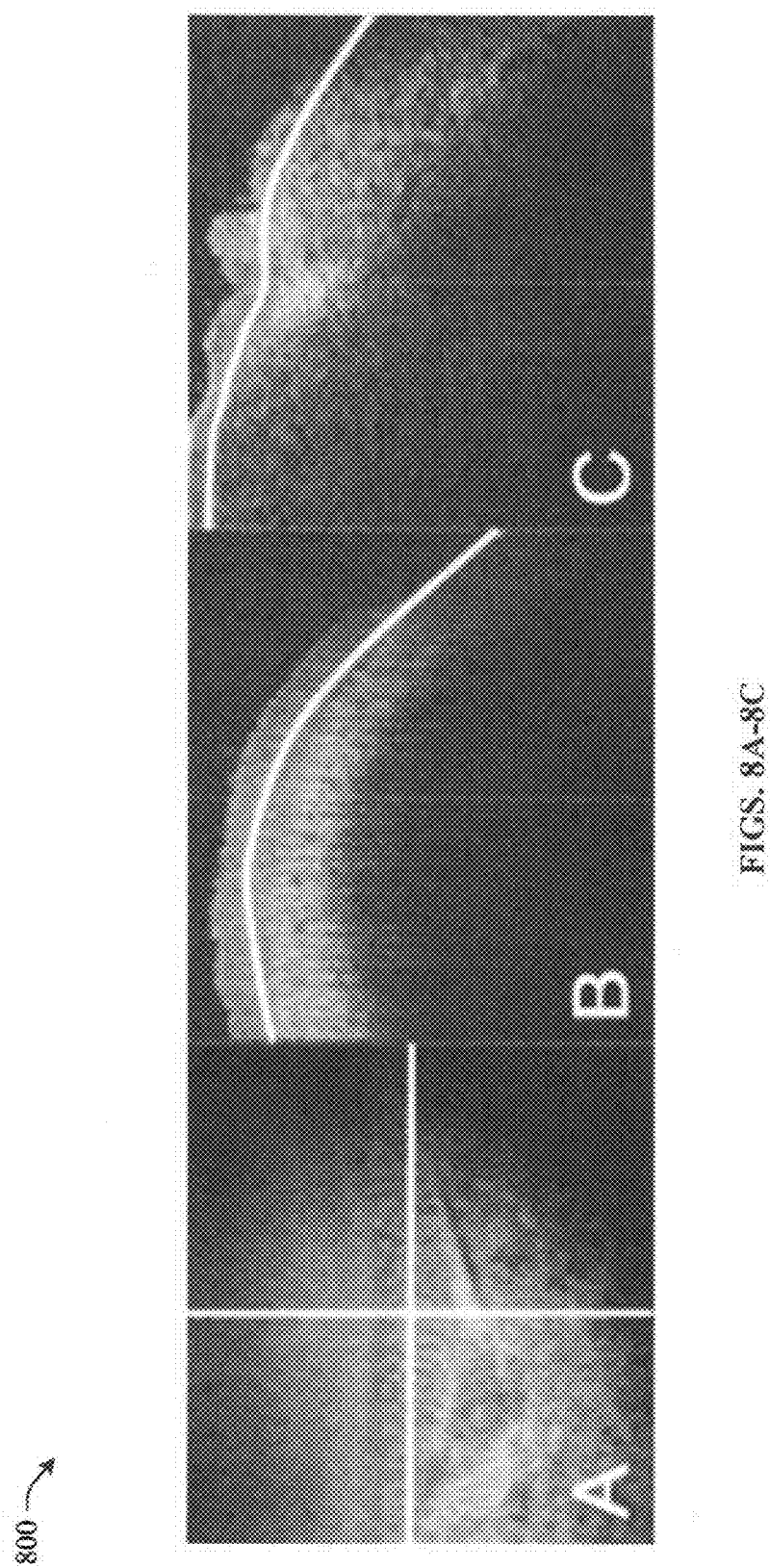
FIGS. 8A-8C are OCT images that are marked (white line) to display the region that will be reconstructed in C-mode images, whereby C-mode imaging allows sectioning along any plane in accordance with aspects of the innovation.

OCT image sets were acquired before or after tissue fixation with no significant difference in image quality. Initial reconstruction and processing in SOCT Browser software included a rolling average to smooth the image. Enface imaging was sometimes able to hint at the underlying structure, but was inadequate for a full understanding of the region. Detailed visualization of the palisade region was conducted with C-mode sectioning which allows data to be sectioned virtually along arbitrary planes and in varying thicknesses relative to the direction of scan acquisition. This allows structures embedded within a volume to be exposed and improves the visualization of pathologic features, as shown in FIGS. 8A-8C. Specifically, FIGS. 8A-8C illustrate images 800 via C-mode imaging, which allows sectioning along any plane to view a tissue, whereby the depth can be adjusted to accommodate the depth of the tissue. FIG. 8A illustrates an enface image with horizontal and vertical axes of orthogonal sections marked. FIG. 8B illustrates a horizontal orthogonal view showing the planes that are included in the enface image in white. FIG. 8C illustrates a vertical view showing the planes that are included in the enface view in white.

Figures 9A, 9B:
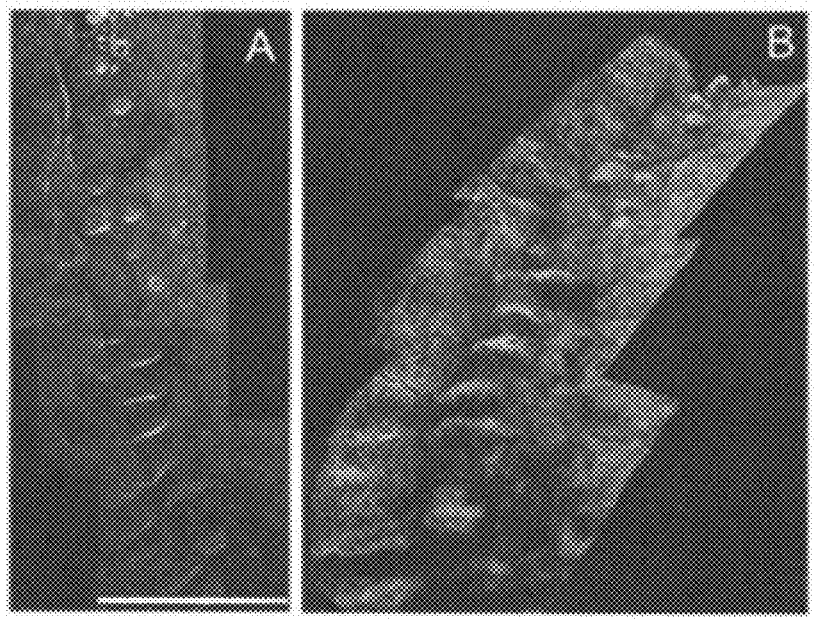
FIGS. 9A-9B are images of serial confocal stacks labeled with collagen VII stitched and reconstructed in 3D in accordance with aspects of the innovation.

The method of mounting the tissue for laser scanning confocal microscopy allowed the acquisition of many contiguous stacks of large areas of tissue without distorting the morphology. These stacks were stitched together to view a large area of the limbus and the reconstructions reveal detailed 3D structure of the palisades that has not previously been well represented, as shown in the images 900 in FIGS. 9A-9B. Specifically, FIG. 9A illustrates the maximum intensity projection through z plane reveals overall limbal structure, where the scale bar equals 635 um. FIG. 9B illustrates the same stack reconstructed in 3D and rotated to show the orientation of structures relative to each other.

Figures 10A, 10B, 10C, 10D, 10E:
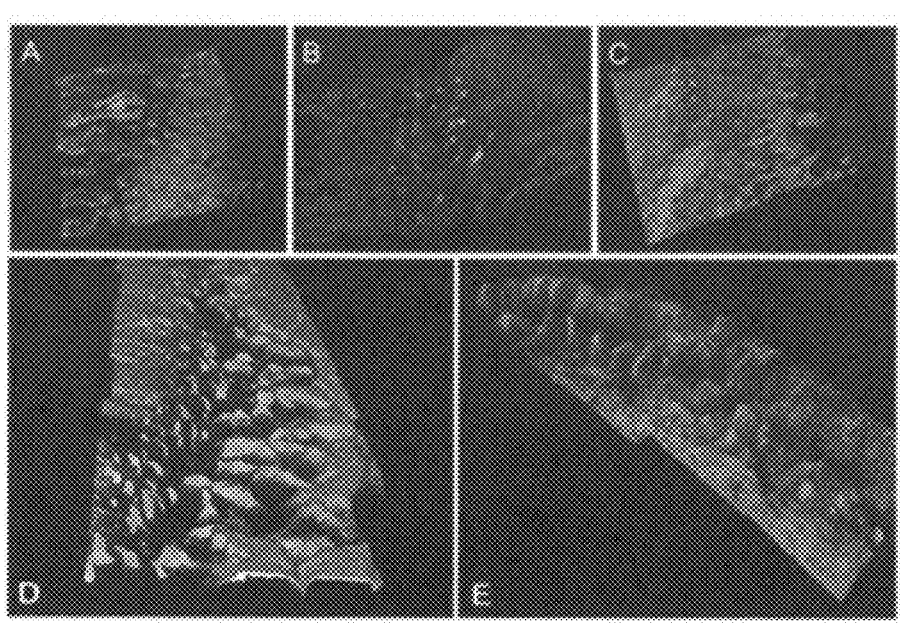
FIGS. 10A-10E are images of 3D confocal reconstructions of different areas of the limbus in accordance with aspects of the innovation.

In addition to presenting the variability of the palisade structures these images reveal the dimension and variability of the limbal structure and the transition of the limbus to the cornea and conjunctiva. When the confocal stacks are reconstructed in 3D or rendered with maximum intensity projections through the stack they reveal a complex and varied structure that demonstrates a wide range of different configurations even within the same subject, as shown in the images 1000 in FIGS. 10A-10E. Specifically, FIGS. 10A-10C illustrate 3D confocal reconstructions of different areas of the limbus from the same subject. FIG. 10D illustrates a 3D reconstruction of a limbal region showing an extensive finger-like pattern. FIG. 10E illustrates a 3D reconstruction of a limbal region showing an undulating and irregular palisade pattern.

All of the observed structures rise from the basement membrane into the epithelium when viewed in 3D. Often ridge-like areas taper off to finger-like projections in lateral and central areas, giving the impression that the finger-like regions are the beginning or end of the ridges. These structures have been described as focal stromal projections. In some areas the ridges are mesh-like while in others they are very clear and rhythmic with some showing many finger-like structures. In some samples, there are very few palisade ridges or just a few of the finger-like structures.

Figures 11A, 11B:
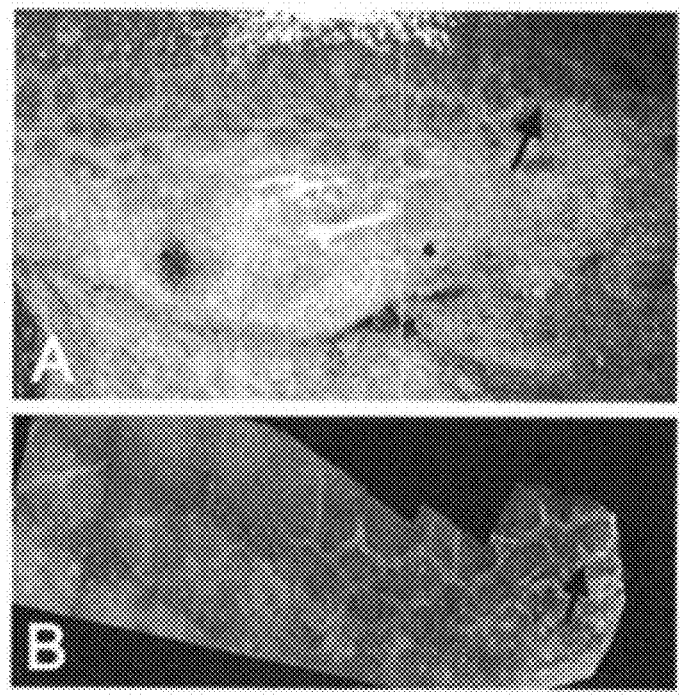
FIGS. 11A-11B are images correlating un-mounted Optical Coherence Tomography and confocal images in accordance with aspects of the innovation.

FIGS. 11A-11B and 12A-12F show images 1100, 1200 respectively of OCT and confocal image stacks were then compared to identify the same regions in each imaging method. The correlation between the methods is clear whether OCT is acquired in unfixed or fixed and mounted tissue. Specifically, FIG. 11A illustrates an un-mounted tissue reconstructed in C-mode imaging showing a mesh-like palisade pattern. FIG. 11B illustrates the same region reconstructed with confocal stacks stitched together. As illustrated in these images, there is a slight change in the angle between the two images because the region was flatter for confocal imaging. The black arrows identify an easily recognizable structure but the whole meshwork can be identified in each image.

Figures 12A, 12B, 12C, 12D, 12E, 12F:
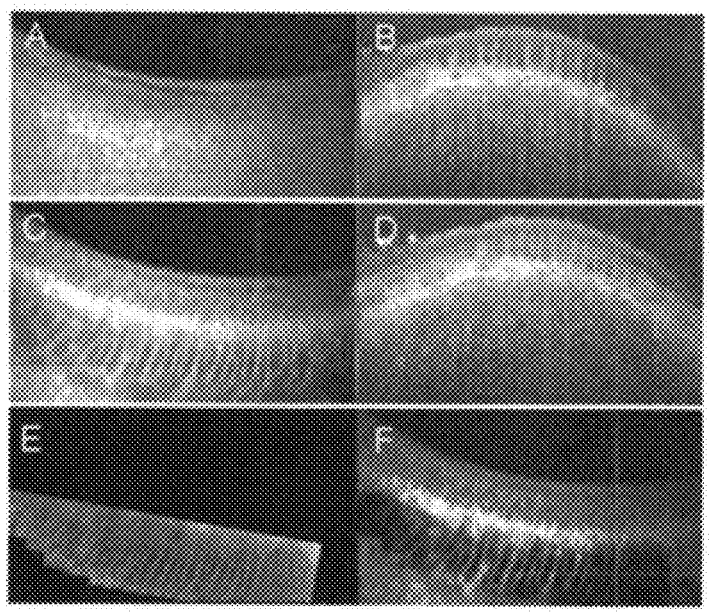
FIGS. 12A-12F are images correlating mounted Optical Coherence Tomography and confocal images in accordance with aspects of the innovation.

FIGS. 12A and 12B illustrate an enface view of tissue and an orthogonal view of tissue at the level of the red line respectively. FIG. 12C illustrates an enface C-mode image reconstructed through the palisade region. FIG. 12D illustrates an orthogonal view of C showing the planes included in the reconstruction. FIG. 12E illustrates a maximum intensity projection of a series of 48 confocal image stacks stitched together to show the same region of the limbus. FIG. 12F illustrates an overlay of OCT enface C-mode image (red) and the confocal maximum intensity stitched image (green). Coincident areas are displayed in yellow. As illustrated in these images there is no distortion between these image sets because they were both acquired from the same mounted tissue.

Reconstruction in 3D reinforces the correlation between the two methods and clearly demonstrates the ability of OCT to reveal detailed and intricate structures in the limbus, as shown in the images 1300 in FIGS. 13A-13C. Specifically, FIGS. 13A and 13B illustrate an enface image of limbal rim and an orthogonal view showing palisade structures respectively. FIG. 13C illustrates a C-mode reconstruction of palisade region showing a very regular palisade pattern in the anterior limbus with an extensive meshwork pattern in the posterior limbus.

These same image sets can be reconstructed in to 3D volumetric models which provide more information about the depth of the palisades and their relationship to each other, as shown in the images 1400 in FIGS. 14A-14C. Specifically, FIG. 14A is a 3D Reconstruction of OCT image set showing palisade pattern. FIG. 14B is a 3D reconstruction of confocal microscopy stack set showing the same region. FIG. 14C illustrates a maximum intensity projection of the area shown in B.

Figures 15A, 15B, 15C, 15D, 15E, 15F:
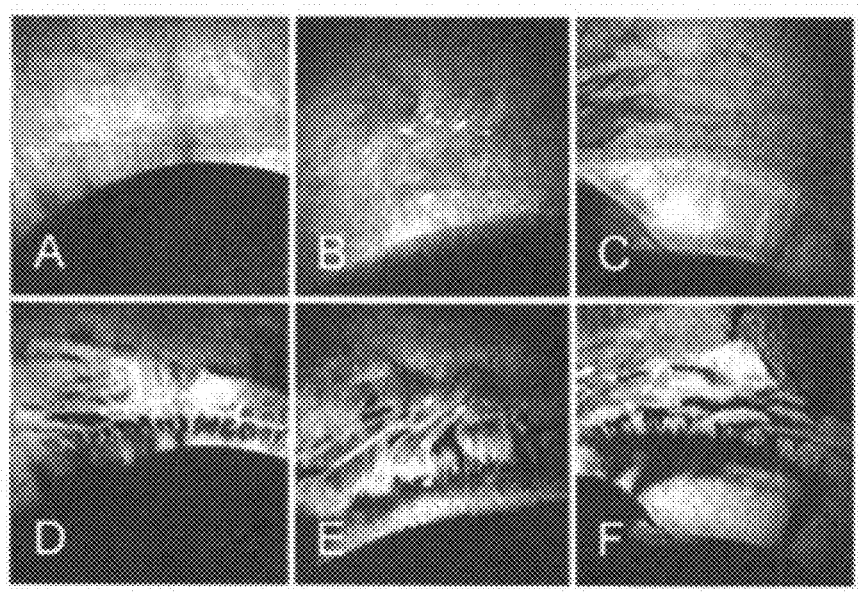
FIGS. 15A-15C are enface views of the corneo-limbal surface acquired with OCT.
FIGS. 15D-15F are examples of C-mode reconstructions of palisades of Vogt patterns derived from the same image volumes displayed in FIGS. 15A-15C in accordance with aspects of the innovation.

Volumetric data sets provide more information about the limbus than has previously been available. The overall pattern of the palisades can be viewed, as shown in in the images 1500 in FIGS. 15A-15F, and the zoom level increased to provide a more restricted field with greater detail. Specifically, FIGS. 15A-15C are enface views of the surface of the tissue. FIGS. 15D-15E are C-mode views of the corresponding palisade regions showing a wide variety of palisade patterns. Reviewing of volume data sets can also provide information about how tissue is being handled and the integrity of different tissue layers.

Figures 16A, 16B, 16C, 16D, 16E, 16F:
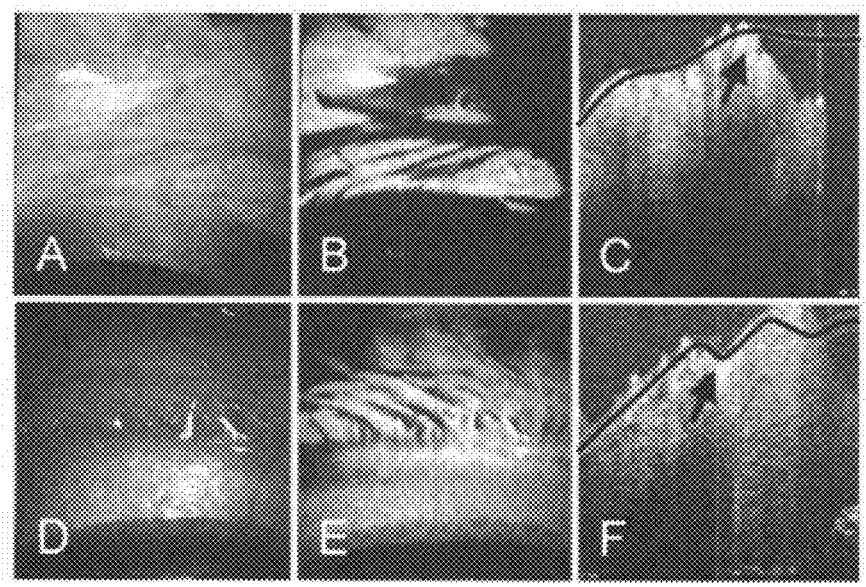
FIGS. 16A-16C are enface views of the corneo-limbal surface acquired with OCT in accordance with aspects of the innovation.
FIGS. 16D-16F are examples of C-mode reconstructions of possible areas of clipped palisades of Vogt derived from the same image volumes displayed in FIGS. 16A-16C in accordance with aspects of the innovation.

In some instances reconstruction revealed palisade areas that extended all the way to the cut edge of the cornea, as shown in the images 1600 in FIGS. 16A-16F. Specifically, FIGS. 16A and 16D are enface views showing the cut edge, which is not perpendicular to the surface of the cornea. From this angle it does not appear that there has been any clipping. FIGS. 16B and 16E are C-mode reconstructions at the level of the palisades showing palisade structures coming right up to and ending abruptly at the cut edge. FIGS. 16C and 16F are vertical orthogonal views of the same section showing the cut edge of the cornea. The planes of the c-mode display are marked in black and the area of the cut edge is highlighted with a black arrow. These cuts are stepped in two stages.

Direct visualization of the corneal epithelial stem cells in vitro is not currently possible, but since the palisades provide the environment necessary for the survival of these cells they can be used as a general indicator of the overall health of the limbus and presence of stem cells. Others have reported three distinct palisade patterns; a standard pattern, an exaggerated pattern, and an attenuated pattern. The patterns disclosed herein fall generally into these three categories, but it is likely that further characterization of the palisade structures may produce finer distinctions in both types and overall dimension of the structures. This study and others clearly illustrate the need to develop a deeper understanding of the architecture of the palisades and define the relationship of that structure to a functional stem cell population. Here, the rapid acquisition of images with OCT allowed acquisition of 3D volumes that encompass large areas of the limbus, providing image sets that can be acquired from living patients and are not available with other imaging technologies. Other imaging methods have distinct limitations when working with a structure as dynamic as the limbus; they cannot describe the overall structure of the palisades and cannot effectively evaluate changes in the palisades over time. Observation and classification of overall palisade patterns requires these macroscopic views and the convenience and speed of OCT imaging makes clinical recording and tracking of palisade structures possible for the first time.

Image sets acquired with OCT and reconstructed with C-mode imaging in the present study provided a complex, detailed representation of this unique structure and revealed it to be more intricate than previously described. Likewise, 3D reconstructions from laser scanning confocal imaging also provided a detailed and complex portrait of this perplexing region and underscored the necessity of 3D visualization of the palisades and the need for further understanding of the structure, function and interactions therein. Areas with distinct, clear structures could be matched between the two imaging modalities to demonstrate that OCT does image the palisades. However, the posterior palisade area was sometimes very convoluted and in some instances extended deeper than confocal microscopy could penetrate. In these areas OCT was able to provide a more accurate representation of the palisade structure, as shown in FIGS. 13A-13C and 15A-15F, and the folding is very complex. Orthogonal images could be found but it is not yet clear whether true crypts are depicted or whether these shapes are created by the intricate folds.

The non-contact nature and speed of OCT imaging could greatly facilitate future studies of the palisades. These investigations can reveal details of the anatomical status and changes in the limbus and allow correlation between those changes with different disease processes, with post-surgical remodeling and restoration of the palisades and in normal aging. Investigation into the palisade structure present in children and young adults could facilitate the understanding of developmental changes in the palisades. OCT imaging has the potential to enable researchers to interpret the significance of the palisade structure in relation to different conditions and determine the impact of variations in the size and pattern of palisades on corneal physiology. In the clinic, visualization of the full dimension of the palisades of individual patients could allow temporal tracking of changes in the palisades. Evaluation of the entire corneal stem cell niche of a donor eye prior to harvesting for autograft would allow better harvesting and enhance targeted biopsies and help to ensure the health of the donor eye. For patients with full LSCD this might allow the success of their limbal transplant to be assessed prior to corneal transplant. Following corneal surgery, OCT evaluation of the palisades could provide a window of opportunity to preemptively diagnose and intervene to treat transplants in danger of failure. Further investigation into the distinctions between different palisade configurations could reveal remodeling patterns in the palisades that are indicative of different conditions and this could potentially become an early diagnostic tool. The image processing used in this study to view selective en-face fields of the limbus was all conducted post-processing and while this is acceptable for research, development of analysis tools and software that allow real-time selective en-face reconstruction of this specific region will make OCT an even more valuable clinical and surgical tool.

During imaging studies many of the limbal rims that were available post-transplantation were not useful for full reconstruction and description of the 3D morphology because the anterior palisade region had been clipped during harvesting of the corneal button. This could simply be due to handling during punching of the button and processing prior to surgery, or the button may have been rejected for transplant after being punched. However, it is possible that the unintentional transplantation of small anterior portions of the limbal palisades has an effect on the post-surgical success of corneal transplants and this possibility bears further investigation.

Development of this technique as a way to visualize the palisades rapidly, in-vivo, and without direct eye contact will provide clinicians a valuable tool for monitoring patients with LSCD and for assessing survival of limbal stem cell transplants. Evaluation of the entire corneal stem cell niche will allow targeted biopsies which should require less tissue and help to ensure the safety of the donor eye. Furthermore, this technique may allow early diagnosis of declining stem cell populations and allow early intervention. Conjunctivalization is currently the most reliable indicator of LSCD because other conditions may cause vascularization and inflammation, but earlier diagnosis of LSCD with OCT may allow intervention to prevent the advancement of the disease.

Visualization of palisades can assist diagnosis of LSCD, and enable specific biopsy. In future explorations of stem cell niches OCT may prove useful in identifying location in-vivo. Immunofluorescence experiments with limbal tissue to correlate the known structures visible with confocal microscopy and the newly described palisade structure and planned experiments will include acquisition and analysis of images acquired with both OCT and confocal microscopy on the same eye.

In summary, the innovation disclosed herein, specifically, OCT, is able to safely, rapidly and effectively image the palisades of Vogt without direct contact to the eye. Thus, the innovation has the potential to enhance an understanding of this stem cell niche, allow development of new clinical and research techniques and assist in developing a better understanding of the scope and function of corneal epithelial stem cell niche. Further, OCT has the potential to characterize the architecture of the palisades in vivo, more accurately harvest stem cells for transplantation, track palisade structures for better diagnosis, follow-up and staging of treatment, and to assess and intervene in the progression of stem cell depletion by monitoring changes in the structure of the palisades.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of imaging palisades of Vogt comprising:
   imaging the palisades of Vogt via a non-contact in-vivo or ex-vivo process to acquire an image, wherein the imaging the palisades of Vogt via a non-contact in-vivo process to acquire the image comprises acquiring high-resolution images rapidly at a predetermined distance from a patient by directing laser light at a corneal limbus of the patient and measuring a delay caused by reflection of the laser light from the corneal limbus, wherein recognition of tissue boundaries depends on contrast between backscattered and/or reflected signal strength;
   transferring the image to an analyzing component;
   identifying in the analyzing component structures represented in the image to determine a status of the image; and
   storing the image in a data storage component for future evaluation or comparison.

2. The method of claim 1, wherein imaging the palisades of Vogt via a non-contact in-vivo or ex-vivo process comprises Optical Coherence Tomography.

3. The method of claim 2, wherein prior to storing the image in the data storage component for future evaluation, the method further comprises monitoring the image to determine a trend represented by data within the image.

4. The method of claim 3, wherein the monitoring the image to determine the trend represented by the data within the image comprises taking a plurality of images over a period of time and comparing a new image with the plurality of images stored in the data storage component to a the prognosis and/or progress of the patient.

5. The method of claim 2, wherein the identifying the structures represented in the image comprises determining whether the image reflects healthy tissue or unhealthy tissue or determining whether the image reflects that tissue that is suitable for donation.

6. A system for imaging palisades of Vogt comprising:
an imaging component to capture non-contact images of the palisades of Vogt;
an analysis component to analyze the images; and
a data storage component to store the images for further evaluation,
wherein the images are captured in the imaging component by acquiring high-resolution images rapidly at a predetermined distance from a patient by directing laser light at a corneal limbus of the patient and measuring a delay caused by reflection of the laser light from the corneal limbus, wherein recognition of tissue boundaries depends on contrast between backscattered and/or reflected signal strength.

7. The system of claim 6, wherein the imaging component comprises an Optical Coherence Tomography system.

8. The system of claim 7, wherein imaging the palisades of Vogt is an in-vivo or ex-vivo process.

9. The system of claim 8, wherein the analysis component includes:
an identification component to determine if the images are from a healthy or an unhealthy patient;
a classification component to classify the images in one of a plurality of categories based on the identification determination of the images; and
a monitoring component to monitor the health of the patient by comparing a new image with the images stored in the data storage component.

10. The system of claim 9, wherein the monitoring component is structured to display the images on a display screen or as a projection in real time during medical procedures.

11. The system of claim 9, wherein the classification component further automatically classifies the images in one of the pluralities of categories by comparing a new image with stored images in the data storage component.

12. The system of claim 9, wherein the classification component further manually identifies normal and abnormal characteristics abnormalities and classifies the images in a specialized category for further evaluation.

13. The method of claim 1, wherein the acquiring comprises scanning at speeds up to 400,000 axial scans per second.

14. The method of claim 13, wherein the acquiring comprises using an Optical Coherence Tomography system.

15. The method of claim 14, further comprising reconstructing the high-resolution images using C-mode slicing.

16. The method of claim 15, further comprising reconstructing the high-resolution images using 3D modeling.

17. A method of imaging palisades of Vogt comprising:
imaging the palisades of Vogt via a non-contact in-vivo or ex-vivo process to acquire an image, wherein the imaging the palisades of Vogt comprises acquiring an Optical Coherence Tomography (OCT) image volume set, analyzing the OCT image volume set using C-mode slicing to reconstruct an area of a corneal epithelial basement membrane of the patient and reconstructing a corneal limbal region of the patient from the OCT image volume set using 3D modeling to reveal a configuration of the palisades of Vogt;
transferring the image to an analyzing component;
identifying in the analyzing component structures represented in the image to determine a status of the image; and
storing the image in a data storage component for future evaluation or comparison.

18. A method of imaging palisades of Vogt comprising:
imaging the palisades of Vogt via a non-contact in-vivo or ex-vivo process to acquire an image, wherein the imaging the palisades of Vogt comprises acquiring an Optical Coherence Tomography (OCT) image volume set, and reconstructing the image using C-mode slicing including sectioning data virtually along multiple planes in the image volume set and in varying thicknesses relative to a direction of scan acquisition of the image volume set;
transferring the image to an analyzing component;
identifying in the analyzing component structures represented in the image to determine a status of the image; and
storing the image in a data storage component for future evaluation or comparison.

19. A system for imaging palisades of Vogt comprising:
an imaging component to capture non-contact images of the palisades of Vogt;
an analysis component to analyze the images; and
a data storage component to store the images for further evaluation,
wherein the images are captured in the imaging component by acquiring an Optical Coherence Tomography (OCT) image volume set, analyzing the OCT image volume set using C-mode slicing to reconstruct an area of a corneal epithelial basement membrane of the patient and reconstructing a corneal limbal region of the patient from the OCT image volume set using 3D modeling to reveal a configuration of the palisades of Vogt.

20. A system for imaging palisades of Vogt comprising:
an imaging component to capture non-contact images of the palisades of Vogt;
an analysis component to analyze the images; and
a data storage component to store the images for further evaluation,
wherein the images are captured in the imaging component by acquiring an Optical Coherence Tomography (OCT) image volume set, and reconstructing the images using C-mode slicing including sectioning data virtually along multiple planes in the image volume set and in varying thicknesses relative to a direction of scan acquisition of the image volume set.

* * * * *

UNITED STATES PATENT AND TRADEMARK OFFICE
CERTIFICATE OF CORRECTION

PATENT NO. : 10,136,808 B2
APPLICATION NO. : 15/676067
DATED : November 27, 2018
INVENTOR(S) : Kira Lynn Lathrop et al.

It is certified that error appears in the above-identified patent and that said Letters Patent is hereby corrected as shown below:

In the Specification

Column 1, Lines 30-33, "This invention was made with government support under EY08098 and EY03263 awarded by the National Institutes of Health (NIH). The government has certain rights in the invention." should read --This invention was made with government support under grant numbers EY008098 and EY003263 awarded by the National Institutes of Health. The government has certain rights in the invention.--.
Column 5, Line 62, "and the" should read --and then--.
Column 7, Line 52, "a large an area" should read --a large area--.
Column 11, Line 63, "shown in in the" should read --shown in the--.

In the Claims

Column 14, Line 61, Claim 5, "to a the" should read --to a--.

Signed and Sealed this
Tenth Day of September, 2019

Andrei Iancu
*Director of the United States Patent and Trademark Office*